United States Patent
Sughrue et al.

(10) Patent No.: US 11,335,453 B1
(45) Date of Patent: May 17, 2022

(54) SYSTEMS AND METHODS FOR DISPLAYING HUBS IN BRAIN DATA

(71) Applicant: Omniscient Neurotechnology Pty Limited, Sydney (AU)

(72) Inventors: Michael Edward Sughrue, Brighton Le Sands (AU); Stephane Philippe Doyen, Mount Kuring Gai (AU); Peter James Nicholas, South Hurstville (AU); Xinling Jiang, Willoughby (AU)

(73) Assignee: Omniscient Neurotechnology Pty Limited, Sydney (AU)

(*) Notice: Subject to any disclaimer, the term of this patent is extended or adjusted under 35 U.S.C. 154(b) by 0 days.

(21) Appl. No.: 17/505,441

(22) Filed: Oct. 19, 2021

(51) Int. Cl.
G06K 9/00 (2022.01)
G16H 30/20 (2018.01)
G06T 7/00 (2017.01)
G16H 30/40 (2018.01)

(52) U.S. Cl.
CPC .......... G16H 30/20 (2018.01); G06T 7/0014 (2013.01); G16H 30/40 (2018.01); G06T 2207/30016 (2013.01)

(58) Field of Classification Search
CPC ...... G16H 30/20; G16H 30/40; G06T 7/0014; G06T 2207/30016
See application file for complete search history.

(56) References Cited

U.S. PATENT DOCUMENTS

| | | | |
|---|---|---|---|
| 2016/0038049 A1* | 2/2016 | Geva | A61B 5/7267 600/544 |
| 2020/0005932 A1* | 1/2020 | Butz-Ostendorf | G16H 30/40 |
| 2021/0090257 A1* | 3/2021 | Bhatia | G06T 7/0014 |
| 2021/0272697 A1* | 9/2021 | Apkarian | G16H 10/20 |
| 2021/0358592 A1* | 11/2021 | Sughrue | G16H 30/20 |
| 2021/0358594 A1* | 11/2021 | Mellem | G16H 10/20 |

OTHER PUBLICATIONS

Ahsan et al., "Beyond eloquence and onto centrality: a new paradigm in planning supratentorial neurosurgery," Journal of Neuro-Oncology, Jan. 2020, 146(2):229-238.

* cited by examiner

*Primary Examiner* — Xin Jia
(74) *Attorney, Agent, or Firm* — Fish & Richardson P.C.

(57) ABSTRACT

Methods, systems, and apparatus, including computer programs encoded on computer storage media, for displaying hubs in brain data. One of the methods includes receiving hub data, the hub data comprising anatomical data and connectivity data of at least part of a brain, the connectivity data comprising a first plurality of nodes and a second plurality of edges, each edge of the second plurality of edges connecting a pair of nodes among the first plurality of nodes; forwarding the hub data to a user computer for display; receiving a first user indication requesting a display of unexpected hub data; determining, in response to the first user indication, unexpected hub data comprising nodes that have connectivity outside of a specified threshold; and forwarding the unexpected hub data to the user computer for display.

22 Claims, 11 Drawing Sheets

| Additional Metrics for STSdp | |
|---|---|
| Betweeness Centrality | 25 |
| Modularity | 15 |
| Clustering Coefficient | 35 |
| Betweeness Centrality | 25 |
| Modularity | 15 |
| Clustering Coefficient | 35 |
| Modularity | 15 |

SYSTEMS AND METHODS FOR DISPLAYING HUBS IN BRAIN DATA

BACKGROUND

Technical Field

The present disclosure relates generally to displaying images of a subject's brain, in particular, to displaying images of a brain that shows unexpected structural and/or functional connectivity and allowing user interaction with the displayed images. The present invention also relates to a system, method, and apparatus for displaying brain images that shows unexpected structural and/or functional connectivity, and to a computer program product including a computer readable medium having recorded thereon a computer program for displaying images of a brain that shows unexpected structural and/or functional connectivity and allowing user interaction with the displayed images.

Background

Medical imaging of a brain can provide insights into functional activity and structural connections of a brain. Images generated using medical imaging techniques such as magnetic resonance imaging (MRI) can be used to provide visual representations of structural and functional data of the brain which can facilitate biomedical research, clinical analysis, and medical interventions. Medical images and its related analysis can also be used to establish a database of normal anatomy and physiology to make it possible to identify abnormalities amongst cohorts.

SUMMARY

This specification describes technologies for processing medical images of brains and/or displaying the processed images in a user-interactive brain navigation system (e.g., a graphic user interface). The processed images can be indicative of physiological or pathological information of a brain.

The disclosed technologies can be used by clinicians, other medical professionals, or users to gain insights about structures, connectivity, and centrality in a subject's brain. Based on such insights, the clinicians, other medical professionals, or users can perform improved and more informed diagnosis, treatments, operations, research, or their combinations than with existing systems.

For example, brain surgery can involve making cuts into the brain. In order to perform brain surgery, one can use a brain atlas containing a brain parcellation scheme to guide surgical path to a site of interest in the brain in order to minimize damage to parts other than the site of interest. The brain atlas can include a set of three-dimensional (3D) voxels representing at least a portion of the brain, each voxel can be assigned to one of the parcellations in a parcellation scheme. The parcellation scheme can be described in a coordinate space. The coordinate space can be the Montreal Neurologic Institute (MNI) space. The term "parcellation" can refer to the process of delineating regions of the brain that have similar properties between individuals, such as functional activity, cytoarchitecture, and structural connectivity. The "parcellation" can be a region of the brain (e.g., cortex) that can be shown to have similar properties across individuals, even if the exact boundaries may differ. Parcellating a brain can be a useful mechanism for analyzing neuroimaging data because it can reduce complexity of the brain's activity to a finite number of domains, and such domains can be assumed to play relatively uniform functions.

Parcellations and their interconnectivity can be useful in understanding or analysis of brain functions in the context of a network, in which areas of the brain are interconnected to deliver higher cerebral functions. Among the parcellations, some play an important role in mediating different network connections. These parcellations are likely to be highly influential over the behavior of the network and are in the mainstream of information flow. Such parcellations (also called "hubs") are central in network organization of the brain. Hubs can be indicated using brain centrality, brain connectivity, hub data (also referred to as hubness data) metrics. However, centrality or hub data varies vastly among different individuals even among healthy subjects. Assuming centrality or hub data are identical among all individuals may lead to non-optimal outcomes in the context of neurosurgical interventions. Lack of convenient and easy to understand presentation of centrality and hub data further add extra difficulty for medical professionals who want to utilize such data to improve existing neurosurgical interventions. As such, there is a need to process centrality or hub data and make presentation of such data to medical professionals convenient, efficient, and less complicated to analyze or use.

In general, one innovative aspect of the subject matter described in this specification can be embodied in methods that include the actions of receiving brain hub data including spatially registered anatomical data and the connectivity data; forwarding the hub data to a user computer for display; receiving a user indication requesting a display of unexpected hub data; determining, in response to the first user indication, unexpected hub data; and forwarding the unexpected hub data to the user computer for display.

Another innovative aspect of the subject matter described in this specification can be embodied in methods that include the actions of receiving brain hub data including spatially registered anatomical data and the connectivity data; displaying the hub data; receiving a user indication requesting a display of unexpected hub data; determining, in response to the first user indication, unexpected hub data; and displaying the unexpected hub data.

Other embodiments of this aspect include corresponding computer systems, apparatus, and computer programs recorded on one or more computer storage devices, each configured to perform the actions of the methods. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

As additional description to the embodiments described below, the present disclosure describes the following embodiments.

Embodiment 1 is a method, comprising: receiving hub data, the hub data comprising anatomical data and connectivity data of at least part of a brain, the connectivity data comprising a first plurality of nodes and a second plurality of edges, each edge of the second plurality of edges connecting a pair of nodes among the first plurality of nodes; forwarding the hub data to a user computer for display;

receiving a first user indication requesting a display of unexpected hub data; determining, in response to the first user indication, unexpected hub data comprising nodes that have connectivity outside of a specified threshold; and forwarding the unexpected hub data to the user computer for display.

Embodiment 2 is the method of embodiment 1, wherein receiving the hub data comprises determining the connectivity data and spatially registering the anatomical data with the connectivity data.

Embodiment 3 is the method of embodiments 1 or 2, wherein the anatomical data comprises a brain atlas, a glass brain, a plurality of images obtained using a medical imaging device, or a combination thereof, and wherein one or more nodes or edges comprises a plurality of hubness parameters.

Embodiment 4 is the method of any one of embodiments 1 through 3, wherein each node of the first plurality of nodes is a parcellation comprising one or more voxels in a medical image of the brain.

Embodiment 5 is the method of any one of embodiments 1 through 4, wherein each edge of the second plurality of edges comprises multiple fiber tracts.

Embodiment 6 is the method of any one of embodiments 1 through 5, wherein the connectivity data represents a degree of correlation of activity between a selected node and one or more other nodes of the first plurality of nodes.

Embodiment 7 is the method of any one of embodiments 1 through 6, wherein the nodes that have connectivity outside of the specified threshold comprises the nodes having connectivity below the specified threshold.

Embodiment 8 is the method of any one of embodiments 1 through 7, wherein the nodes that have connectivity outside of the specified threshold comprises the nodes having connectivity above the specified threshold.

Embodiment 9 is the method of any one of embodiments 1 through 8, wherein the anatomical data and the connectivity data are in three dimensions (3D), and the hub data comprises 3D data.

Embodiment 10 is the method of any one of embodiments 1 through 9, wherein the unexpected hub data comprises 3D data.

Embodiment 11 is the method of any one of embodiments 1 through 10, wherein the unexpected hub data further comprises one or more quantitative or qualitative parameters associated with a node, an edge, or a combination thereof.

Embodiment 12 is the method of any one of embodiments 1 through 11, wherein the connectivity data comprises a binary classification for each of the first plurality of nodes.

Embodiment 13 is the method of any one of embodiments 1 through 12, the unexpected hub data includes only nodes that are classified as unexpected.

Embodiment 14 is the method of any one of embodiments 1 through 13, wherein the displayed unexpected hub data is used by a user to make a clinical judgement or decision, comprising one or more of: guiding a surgical procedure; predicting an outcome of the surgical procedure; evaluating risk associated with the surgical procedure; selecting appropriate target for a therapy; and understanding nature of a neurologic deficit in a subject.

Embodiment 15 is the method of any one of embodiments 1 through 14, wherein the method further comprises: receiving a user interaction with the display of the unexpected hub data; determining, in response to the user interaction, an update on the unexpected hub data; and forwarding the update to the user computer for an updated display.

Embodiment 16 is the method of any one of embodiments 1 through 15, wherein the update on the unexpected hub data comprises only a portion of the unexpected hub data.

Embodiment 17 is the method of any one of embodiments 1 through 16, wherein the update on the unexpected hub data comprises: a zoom-in of the unexpected hub data, a rotation of the unexpected hub data, a display of a parameter corresponding to a selected node or edge, a change of color of at least part of the unexpected hub data, or a combination thereof.

Embodiment 18 is the method of any one of embodiments 1 through 17, wherein the connectivity data have been spatially registered with the anatomical data, the anatomical data describing anatomy of the at least part of the brain.

Embodiment 19 is the method of any one of embodiments 1 through 18, wherein the first plurality of nodes have specified locations within the anatomy of the at least a part of the brain.

Embodiment 20 is a computer program product, encoded on one or more non-transitory computer storage media, comprising instructions that when executed by one or more computers cause the one or more computers to perform operations comprising: receiving hub data, the hub data comprising anatomical data and connectivity data of at least part of a brain, the connectivity data comprising a first plurality of nodes and a second plurality of edges, each edge of the second plurality of edges connecting a pair of nodes among the first plurality of nodes, the anatomical data and the connectivity data being spatially registered relative to each other; forwarding the hub data to a user computer for display; receiving a first user indication requesting a display of unexpected hub data; determining, in response to the first user indication, unexpected hub data comprising nodes that have connectivity outside of a specified threshold; and forwarding the unexpected hub data to the user computer for display.

Embodiment 21 is one or more non-transitory computer storage media encoded with computer program instructions that when executed by one or more computers cause the one or more computers to perform operations comprising: receiving hub data, the hub data comprising anatomical data and connectivity data of at least part of a brain, the connectivity data comprising a first plurality of nodes and a second plurality of edges, each edge of the second plurality of edges connecting a pair of nodes among the first plurality of nodes, the anatomical data and the connectivity data being spatially registered relative to each other; forwarding the hub data to a user computer for display; receiving a first user indication requesting a display of unexpected hub data; determining, in response to the first user indication, unexpected hub data comprising nodes that have connectivity outside of a specified threshold; and forwarding the unexpected hub data to the user computer for display.

Embodiment 22 is a system comprising: one or more computers and one or more storage devices on which are stored instructions that are operable, when executed by the one or more computers, to cause the one or more computers to perform operations comprising: receiving hub data, the hub data comprising anatomical data and connectivity data of at least part of a brain, the connectivity data comprising a first plurality of nodes and a second plurality of edges, each edge of the second plurality of edges connecting a pair of nodes among the first plurality of nodes, the anatomical data and the connectivity data being spatially registered relative to each other; forwarding the hub data to a user computer for display; receiving a first user indication requesting a display of unexpected hub data; determining, in response to the first user indication, unexpected hub data comprising nodes that have connectivity outside of a specified threshold; and forwarding the unexpected hub data to the user computer for display.

Present systems or methods that generate or present the centrality or hubness data can be cumbersome to use and operate, and typically produce outputs that lack clinical usefulness. The subject matter described in this specification can be implemented in particular embodiments so as to realize numerous advantages over existing systems and methods. For example, the disclosed technologies can provide a technical solution for medical professionals or other users to a technical problem of presenting clinically useful centrality and hubness data of the brain with an easy-to-use interface and allow users to glean insights about a subject's brain. The interface can be an interactive, user-friendly graphical user interface (GUI) that facilitates customized visualization.

The disclosed technologies can process images of the brain and output hubness data with convenient customization for visualization. For example, the subject matter herein advantageously allows simultaneous visualization of (i) spatial locations of brain hubs relative to anatomical structures in the brain, e.g., spatial relationship of the nodes and/or edges relative to brain structure(s) that are in question, e.g., in a planned surgical procedure; (ii) classification of brain hubs with customized threshold(s), e.g., unexpected nodes and edges can be show at a different color from the normal nodes and edges; and (iii) quantitative parameters and metrics of any user-selected hubs of the brain.

The simultaneous visualization of various characterizations of the brain hub data can provide the user a comprehensive understanding of the subject's brain connectivity and centrality information. As a result, the disclosed technologies can advantageously allow a user to make clinical determinations by visualization of the centrality or hubness data. The disclosed technologies can be used by users in: guiding a surgical procedure; predicting an outcome of the surgical procedure, evaluating risk associated with the surgical procedure, selecting appropriate target(s) in a brain for a therapy; and understanding nature of a neurologic deficit in a subject. For example, a medical professional can gain insight about the unexpected hubness of a patient's brain, either above or below a reference hubness among normal people, and such insight can be used to determine a surgical path that may minimize or avoid damage to the specific brain in question.

The details of one or more variations of the subject matter described herein are set forth in the accompanying drawings and the description below. Other features and advantages of the subject matter described herein will be apparent from the description, drawings, and claims.

BRIEF DESCRIPTION OF THE DRAWINGS

Like reference symbols in various drawings indicate like elements.

DETAILED DESCRIPTION

Figure 1:
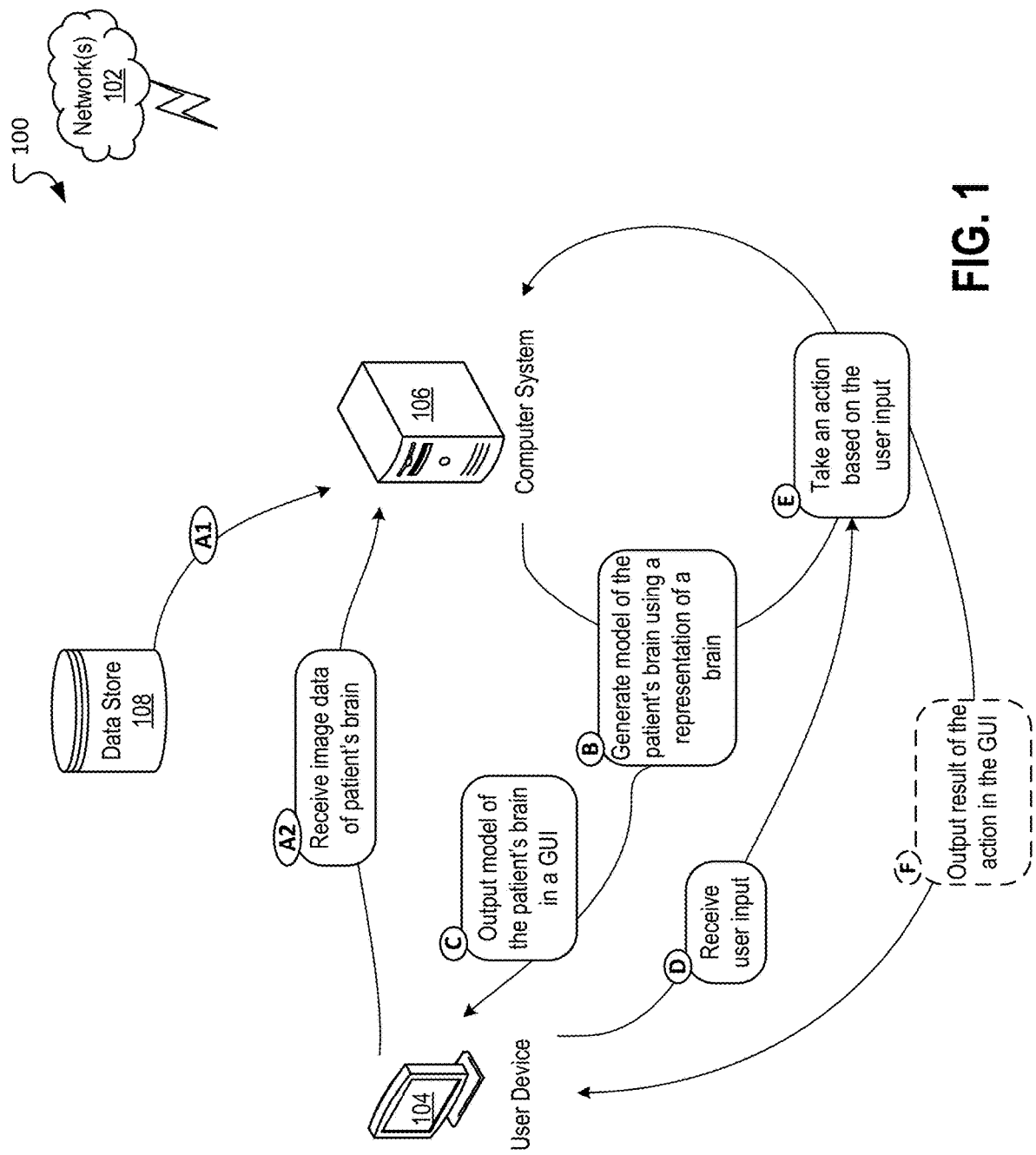
FIG. 1 is a conceptual diagram illustrating a computing environment for generating a GUI representation of a brain.

FIG. 1 is a schematic diagram illustrating a computing environment 100 for generating a GUI representation of a brain. The computing environment 100 can include a user device 104, a computer system 106, a data store 108, and a medical imaging device 110, which can communicate (e.g., wired and/or wirelessly) via network(s) 102.

The user device 104 can be used by a medical professional, such as a clinician, surgeon, doctor, nurse, researcher, or other professional. The user device 104 and technologies described herein can be used by any other user. The user device 104 can be any one of a computer, laptop, tablet, mobile device, mobile phone, and/or smartphone. Sometimes, the user device 104 can be integrated into or otherwise part of one or more other devices in a medical setting, such as the medical imaging device 110 and/or the computer system 106. The medical professional can use the user device 104 to view information about the brain. For example, using the disclosed technology, the medical professional can view, at the user device 104, 3D representations of the brain and make determinations about what diagnosis, treatment, and/or surgical procedures to perform. The medical professional can also view other/additional information about the particular patient at the user device 104 to make more informed decisions with regards to the particular patient's diagnosis, treatment, surgery, or other medical or research purposes. Thus, the user device 104 can provide hardware that can support the GUIs, software, and applications described herein, such as a singular and interactive brain navigation system that makes it easier and more intuitive for the medical professionals to make medical and research determinations.

The computer system 106 can be a remote computing system, a cloud-based system or service, and/or integrated with or otherwise part of one or more devices in a medical setting (e.g., such as the user device 104 and/or the medical imaging device 110). The computer system 106 can be a computer, processor, a network of computers, a server, and/or a network of servers. Sometimes, each medical setting (e.g. a hospital) can have one or more computer systems 106. Sometimes, the computer system 106 can be used across multiple medical settings (e.g., multiple hospitals). The computer system 106 can be configured to generate interactive representations of patients' brains based on image data of the brains. The computer system 106 can also generate GUIs to display the interactive representations of the brains at the user device 104.

Sometimes, the computer system 106 can clean the image data by removing personally identifying information (e.g., protected health information (PHI)) from that data. Cleaning the image data can be beneficial to preserve patient privacy, especially if the interactive representations of patients' brains are used for medical research, clinical studies, or otherwise are stored in the data store 108 for future retrieval and use. Removing personally identifying information can also be advantageous if the computer system 106 is remote from the user device 104 and the interactive representations of the brain are generated at the computer system 106 that is outside a secure hospital infrastructure or other network where the image data may be generated and/or the interactive representations of the brain may be outputted. In other words, removing personally identifying information can be advantageous to preserve patient privacy when patient data is communicated between different networks and/or infrastructure.

The data store 108 can be a remote data store, cloud-based, or integrated into or otherwise part of one or more other components in the medical setting (e.g., such as the user device 104 and/or the computer system 106). The data store 108 can store different types of information, including but not limited to image data of patient brains (e.g., from the medical imaging device 110), cleaned image data (e.g., from the computer system 106), 3D representations of patient brains or other interactive representations of patient brains (e.g., from the computer system 106), connectivity data associated with patient brains, determinations, actions, or other user input taken by the medical professional (e.g., at the user device 104), patient information or records, or other relevant information that can be used in a medical setting.

The medical imaging device 110 can be any type of device and/or system that is used in the medical setting to capture image data of patient brains. The medical imaging device 110 can capture image data that includes but is not limited to x-rays, computed tomography (CT) scans, magnetic resonance imaging (Mills), and/or ultrasound. One or more other types of image data can also be captured by the medical imaging device 110. The computer system 106 can be configured to receive any type of image data of a brain and generate connectivity data about the brain from that image data to map the data onto a user-friendly interactive representation of the brain.

Figure 2:
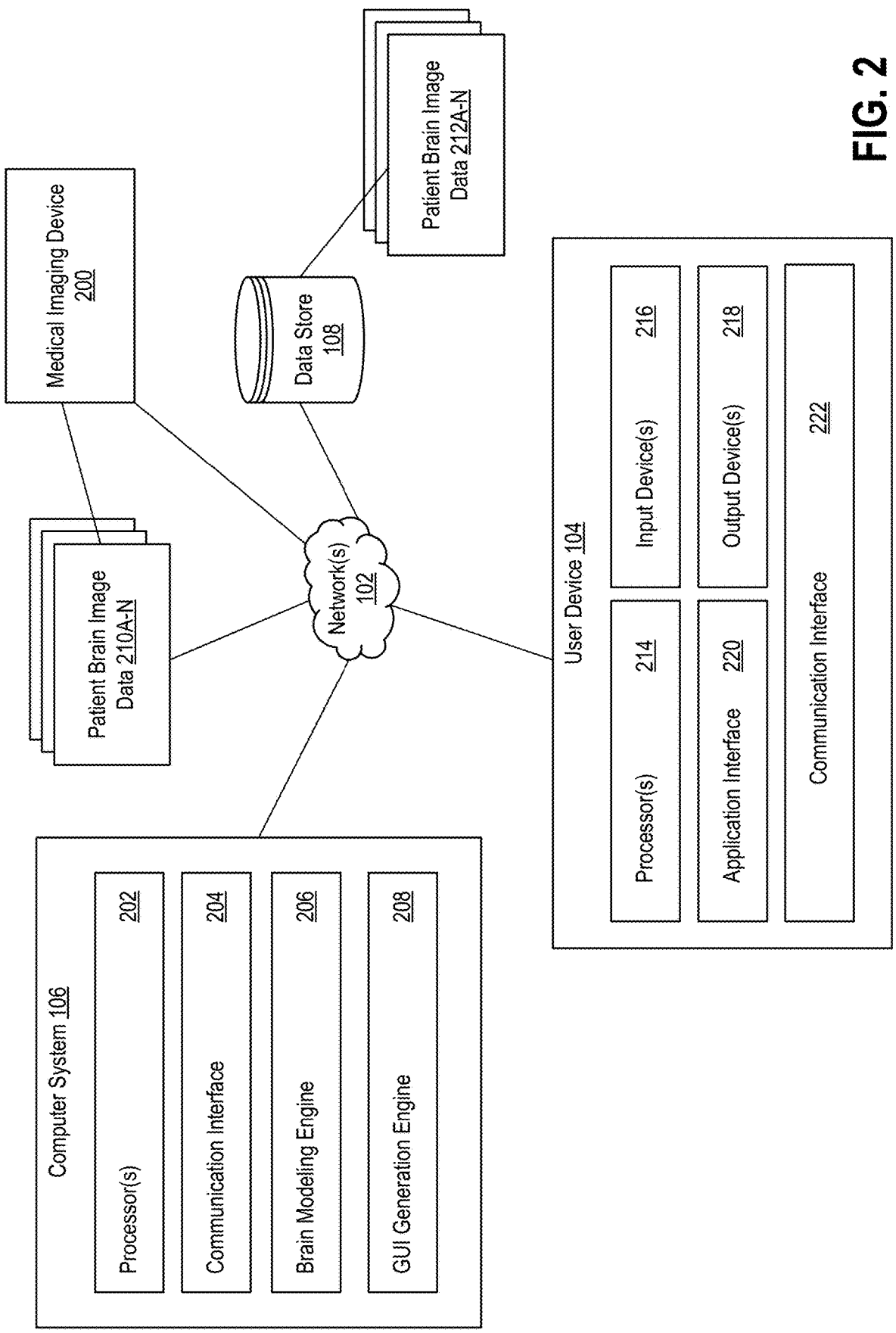
FIG. 2 illustrates components in a computing landscape that can be used to generate the GUI representation of the brain.

Referring to FIGS. 1 and 2, the computer system 106 can receive image data of the brain from one or more of the data store 108 (step A1), the user device 104 (step A2), and the medical imaging device 200. Sometimes, for example, when the user device 104 is part of the medical imaging device 200, the computer system can receive the image data captured by the medical imaging device 200 from only one device (e.g., the medical imaging device 200 or the user device 104). The image data can be captured by the medical imaging device 200 then sent directly, in real-time, to the computer system 106 for real-time processing. Sometimes, the image data can be captured by the medical imaging device 200, then initially reviewed by the medical professional at the user device 104. Accordingly, the user device 104 can transmit the image data to the computer system 106 (step A2).

In some implementations, image data of multiple different brains can be captured by multiple different medical imaging devices 200. The image data can be stored in the data store 108 for future processing and analysis. The computer system 106 can then retrieve a batch or batches of the image data from the data store 108 and batch process the image data. Batch processing can be advantageous to use fewer computational resources and reduce network bandwidth.

Once the computer system 106 receives the image data (e.g., steps A1-A2), the computer system can generate a model of the brain using a representation of a brain (step B).

For example, the computer system 106 can map or model the patient's brain from the image data onto a 3D representation of a brain. The 3D representation can be a generic brain in 3-dimensional or other multi-dimensional space or it can be an anatomical representation of the particular patient's brain. The 3D representation can be a glass brain. Mapping the patient's brain onto the glass brain can be advantageous to provide vantage points of different structures, parcellations, and connectivity in the particular patient's brain. A medical professional can more easily analyze the particular patient's brain via the 3D representation of the brain rather than through the raw image data captured by the medical imaging device 110. As a result, the medical professional can generate more informed decisions and determinations with regards to the particular patient's diagnosis, treatment, surgery, condition, or other medical or research purposes.

Once the patient's brain is modeled using the representation of the brain (step B), the computer system 106 can output the model of the patient's brain to a GUI at the user device 104 (step C). For example, the computer system 106 can generate GUI data representing a model of the patient's brain and then transmit the GUI data to the user device 104 to be processed for display. The model can represent the patient's brain overlaid on the glass brain. Sometimes, instead of outputting the model at the user device 104 (step C), the computer system 106 can store the model of the patient's brain in the data store 108. The model of the patient's brain can then be accessed/retrieved at a later time and presented to a medical professional or other user at the user device 104.

As mentioned throughout, when the model of the patient's brain is outputted at the user device 104, the GUI can allow the medical professional to take numerous actions in response to reviewing the model of the patient's brain. For example, the medical professional can determine what type of diagnosis, treatment, or surgical procedures to take with regards to this particular patient. The medical professional can also interact with the model of the patient's brain through use-selectable options and features in the GUI that is outputted at the user device 104. The medical professional can change views of the model of the patient's brain (e.g., rotate around the model, view only a left or right side of the patient's brain, etc.), select portions of the patient's brain from the model (e.g., select a particular lobe, node, parcellation, etc.), view other information about the patient (e.g., health records, prior medical visits, etc.), and simulate surgical procedures that can impact different parcellations or portions of the patient's brain (e.g., slicing a node or nodes that are connected to other nodes in the patient's brain). The medical professional can provide input to the user device 104, for example, via an input device, and the input can indicate the medical professional's interaction(s) with the model of the patient's brain. This input can then be received by the computer system 106 (step D).

The computer system 106 can take an action based on the received user input (step E). For example, if the medical professional changes or selects a different view of the model of the patient's brain, then the computer system 106 can generate an updated GUI data representing the patient's brain that includes the selected view data. This updated GUI data can be processed for display at the user device (step F). As another example, the medical professional can remove one or more nodes from the model of the patient's brain. The computer system 106 can receive this input (step D), simulate removal of the user-selected nodes (step E), then output results of removing such nodes from the brain at the user device 104 (step F). The medical professional can review the output results and take further actions in response. Further actions can include decisions about what nodes the medical professional should remove during the actual medical procedure and/or how to proceed with diagnosis, treatment, and/or the medical procedure.

Sometimes, the computer system 106 can take an action based on the user input (step E) that does not also include outputting a result of the action at the user device 104 (step F). For example, the medical professional can input notes about what actions the medical professional intends to take during a medical procedure, a diagnosis for the particular patient, and/or treatment for the patient. The computer system 106 can receive this input and store it in the data store 108 but may not output results from storing this input. This input can then be retrieved from the data store 108 and provided to one or more other devices (e.g., a report can be generated that indicates the patient's diagnosis and treatment). The report can then be provided to a device of the patient. The report can also be transmitted to devices of other medical professionals, such as those in a hospital infrastructure/network). The computer system 106 can take one or more other actions based on the user input (step E) and optionally output results of the action(s) at the user device 104 (step F).

FIG. 2 illustrates components in a computing landscape that can be used to generate data about the brain. As described above, the user device 104, computer system 106, data store 108, and medical imaging device 110 can communicate via the network(s) 102. One or more of the components 104, 106, 108, and 110 can also be integrated into a computing system, network of devices, server, cloud-based service, etc. The network(s) 102 may be a wide-area network (WAN), such as the Internet, a cellular telecommunications network, or a private WAN. Connection via the network(s) 102 can include a traditional dial-up modem, a high-capacity (e.g., cable) connection such as a broadband modem, and/or a wireless modem.

The computer system 106 can include processor(s) 202, communication interface 204, brain modelling engine 206, and GUI generation engine 208. The processor(s) 202 can be configured to perform one or more operations described herein. Although not depicted, the computer system 106 can also include at least one memory unit, which may have semiconductor random access memory (RAM) and semiconductor read only memory (ROM).

One or more of the techniques and processes described herein can be implemented as software application programs executable by the processor(s) 202 in the computer system 106. Moreover, one or more of the techniques and processes described herein can be executed in browsers at remote terminals, systems, or devices (e.g., the user device 104 and/or another computer system), thereby enabling a user of the remote terminals, systems, or devices to access the software application programs that are executing on the computer system 106. For example, steps for any of the techniques and processes described herein can be effected by instructions in the software application programs that are carried out within the computer system 106. Software instructions may be formed as one or more code modules (e.g., using PYTHON or equivalent language modules installed on the computer system 106 and/or the remote terminals, systems, or devices), each for performing one or more particular tasks. The software instructions can also be divided into separate parts. For example, a first part and the corresponding code module(s) can perform the techniques and processes described herein and a second part and the corresponding code module(s) can manage a user interface (e.g., the GUIs described herein) between the first part and the medical professional at the user device 104.

Moreover, the software may be stored in a non-transitory, tangible, computer readable medium, including storage devices described throughout this disclosure. The software can be loaded into the computer system 106 from the computer readable medium, and then executed by the computer system 106. A computer readable medium having such software or computer program recorded on the computer readable medium can be a computer program product. Examples of transitory or non-tangible computer readable transmission media that may also participate in the provision of software, application programs, instructions and/or data include radio or infra-red transmission channels as well as a network connection to another computer or networked device, and the Internet or Intranets, including e-mail transmissions and information recorded on Websites and the like.

Still referring to the computer system 106, the brain modelling engine 206 can be configured to map a patient's brain onto a representation of a brain (e.g., refer to step B in FIG. 1). For example, the brain modelling engine 206 can receive patient brain image data 210A-N, which can be used to generate a model of the patient's brain. The patient brain image data 210A-N can be received from the medical imaging device 110. The patient brain image data 210A-N can also be received from the user device 104. In some implementations, as described in reference to FIG. 1, the computer system 106 can retrieve patient brain image data 212A-N from the data store 108. The patient brain image data 212A-N can then be used by the brain modelling engine 206 to model the patient's brain.

Sometimes, modelling the brain can include identifying connectivity data for the particular brain. Modelling the brain can then include mapping the connectivity data over the representation of a generic brain. In yet some implementations, modelling the patient's brain can include identifying hubs, parcellations, deep nodes, lateral nodes, and other portions of the patient's brain that can be mapped onto the representation of the generic brain. Moreover, the brain modelling engine 206 can be configured to identify personal information in the image data of the brain and extract that information before mapping the patient's brain onto the representation of the generic brain. The brain modelling engine 206 can use one or more machine learning models to accurately map the particular patient's brain data onto a representation of the generic brain.

In some implementations, for example, Digital Imaging and Communications in Medicine (DICOM) images of a particular brain to be parcellated can be processed by the brain modelling engine 206. DICOM is an international standard for transmitting, storing, retrieving, processing and/or displaying medical imaging information. A registration function for the particular brain can be determined in a Montreal Neurological Institute (MNI) space (a common coordinate space) described by a set of standard brain data image sets, a registered atlas from a human connectome project can be determined, and diffusion tractography of the DICOM images can be performed to determine a set of whole brain tractography images of the particular brain (in neuroscience, tractography can be thought of as a 3D modelling technique used to represent tracts, e.g., to represent white matter tracts visually). For each voxel in a particular parcellation in the registered atlas, voxel level tractography vectors showing connectivity of the voxel with voxels in other parcellations can be determined, the voxel can be classified based on the probability of the voxel being part of the particular parcellation, and determining of the voxel level tractography vectors and the classifying of the voxels for all parcellations of the human connectome project multi-modal parcellation version 1.0 (HCP-MMP1) Atlas can be repeated to form a personalised brain atlas (PBs Atlas) containing an adjusted parcellation scheme reflecting the particular brain.

The GUI generation engine 208 can be configured to generate GUI data for the modelled brain. The GUI generation engine 208 can receive the modelled brain from the brain modelling engine 206 and generate appropriate GUI data for displaying the modelled brain to the medical professional (e.g., refer to FIG. 3). The GUI generation engine 208 can also transmit the generated GUI data to the user device 104 to be processed for display to the medical professional.

Moreover, whenever user input is received from the user device 104 that includes performing some action in response to the output model of the brain, the input can be received by the computer system 106. The brain modelling engine 206 can take some action (e.g., refer to step E in FIG. 1) in response to receiving the user input (e.g., refer to step D in FIG. 1). That action can include, for example, simulating removal of one or more nodes in the patient's brain. The GUI generation engine 208 can generate updated GUI data based on the actions taken by the brain modelling engine 206 (e.g., refer to step F in FIG. 1). The GUI generation engine 208 can then transmit the updated GUI data to the user device 104 to be processed for display to the medical professional.

Sometimes, one or more of the components of the computer system 106, such as the brain modelling engine 206 and the GUI generation engine 208 can be part of one or more different systems. For example, the brain modelling engine 206 can be part of a software application program that can be loaded and/or executed at another device, such as the user device 104 and/or the medical imaging device 110. As another example, the GUI generation engine 208 can be part of a software application program that is executed at the user device 104 and the brain modelling engine 206 can be executed at the computer system 106 or another remote computing system, server, or cloud-based server or system.

The user device 104 can include processor(s) 214, input device(s) 216, output device(s) 218, application interface 220, and communication interface 222. The processor(s) 214 can be configured to perform one or more operations described herein. Although not depicted, the user device 104 can also include at least one memory unit, which may have semiconductor random access memory (RAM) and semiconductor read only memory (ROM).

The input device(s) 216 and output device(s) 218 can include one or more of an audio-video interface that couples to a video display, speakers, and/or a microphone, keyboard, mouse, scanner, camera, touch screen display, other display screen(s) (e.g., LCDs), joystick, and/or other human interface device. The input device(s) 216 can be configured to receive user input from the medical professional or other user. The output device(s) 218 can be configured to output the model of the patient's brain and/or actions taken by the computer system 106 in response to the user input. The output device(s) 218 can present a variety of GUI displays and information to the medical professional, where such displays and information are generated by the computer system 106. The output device(s) 218 can also output information that is received or otherwise generated by the medical imaging device 110.

The application interface 220 can be executable software or another program that is deployed at the user device 104.

The GUI data generated by the computer system 106 can be displayed or otherwise outputted via the application interface 220. In some implementations, the application interface 220 can be executed at a browser of the user device 104. The medical professional can then access and view the GUIs via the Internet or other connection. Sometimes, the application interface 220 can be executed as a software module/program/product at the user device 104. The application interface 220 can provide the interactive GUIs to the medical professional and receive input from the medical professional (e.g., FIG. 3).

The communication interfaces 204 and 222 can be configured to provide communication between and amongst the components described herein. For example, a modem can be integrated therein.

Figure 3:
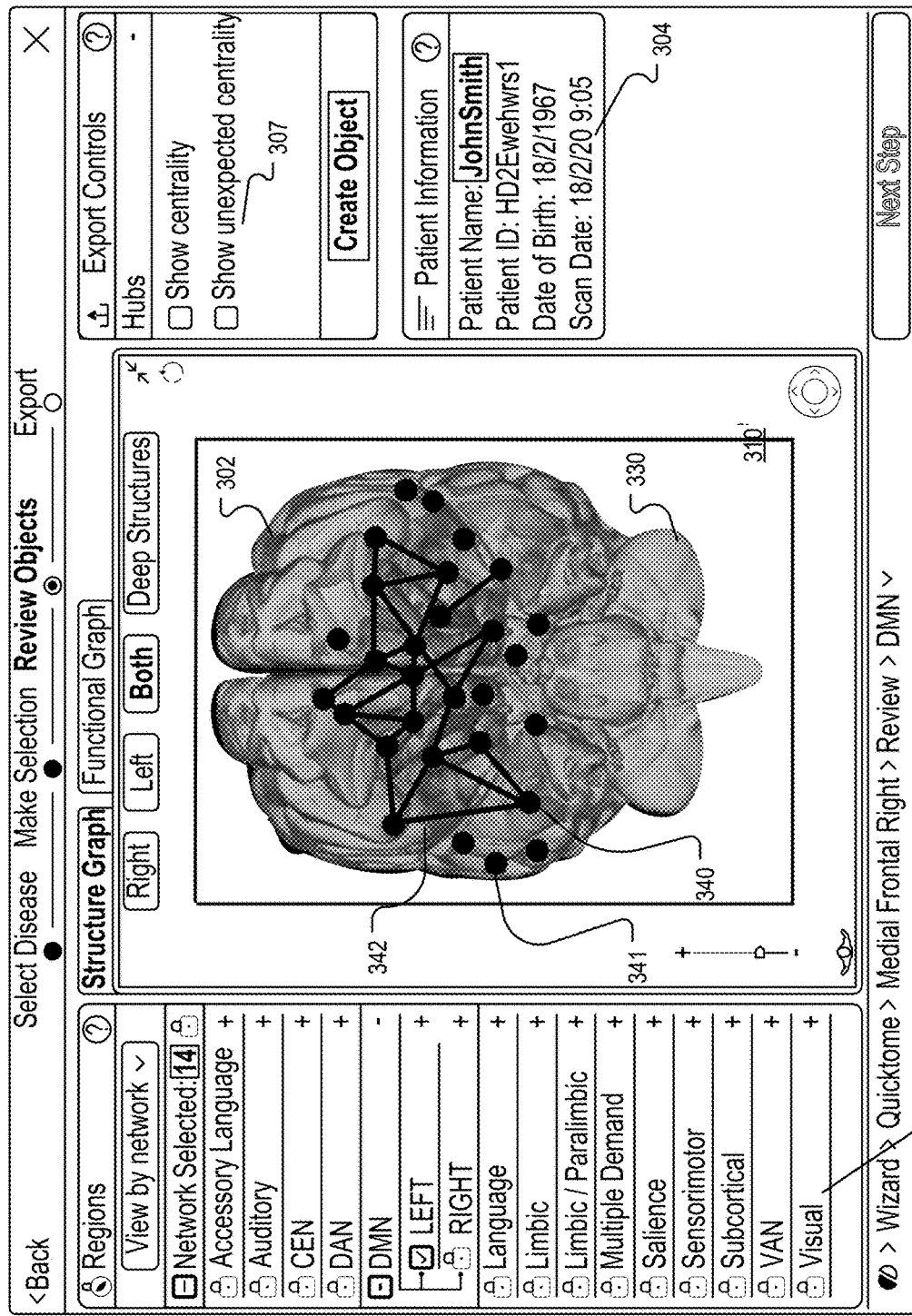
FIG. 3 illustrates an example user-interactive GUI displaying the brain.

FIG. 3 is an example user-interactive GUI. The GUI 300 can be displayed at the user device 104 described herein. The GUI 300 displays processed medical imaging data of a subject's brain within a data display window 310. The processed medical imaging data may be forwarded to a user device 104 by a server or another computer, e.g., the computer system 106 in FIG. 1. The processed medical imaging data may include processed data 302, patient information 304, and selectable options 306 307.

The processed data 302 can include a 3D representation of the brain. Such representation can be generated from any type of medical imaging data that is indicative of anatomical information 330 of the brain. The processed data 302 can include anatomical data of some or all parts of the brain. At least a portion of the processed data 302 may have been processed from "raw" image data acquired at the medical imaging device(s) 110. The processing may include various manipulation or calculation of the "raw" image data, e.g., such as segmentation, registration, histogram, interpolation, filtering, and diffusion tensor calculation.

The processed data 302 may include connectivity data 340 in some or all parts of the brain. The connectivity data 340 may include a first number of brain nodes 341 and a second plurality of edges 342. Each node 341 may represent some predefined collection of brain tissue(s). Some or all nodes can be considered as brain hubs. "Hubness data" or "hub data" is indicative of the level of connection from a region of the brain, e.g., nodes, to other regions. A node 341 can include a single voxel in medical images or a group of voxels. When a group of voxels are included in a node, they may or may not be adjacent to or connected with one or more voxels within the same node. A node 341 can be a parcellation or a group of parcellations. When there are a group of parcellations in a single node, they may or may not be spatially connected with one or more parcellations within the same node. In some cases, each node 341 may be visually represented using a size or shape that corresponds to the number of voxels or parcellations within it. For example, a node represented by a bigger circle in the GUI indicates it is a node with more voxels or parcellations than a smaller circle representing another node. In alternative cases, each node 341 may be visually represented by a uniform size and/or shape as shown in FIG. 3. An edge 342 can measure the functional connectivity between a pair of nodes. An edge 342 may be visually represented by a line connecting two nodes at its opposite ends. In some cases, the level of connectivity of the edge may be visualized using different colors, patterns, or the like.

The anatomical data 330 and the connectivity data 340 of the same brain can be spatially registered or aligned.

The user, e.g., a medical professional, may interact with the processed data 302, the anatomical data 330, the connectivity data 340, and the selectable options 306 307 of the GUI 300. The selectable options 306 307 can be located around the data display window 310 of the GUI 300.

Although a brain image is useful for a user, the user can benefit more if they have additional information about components of the brain that is imaged. This additional information can be advantageous for the user to make more informed decisions with regard to diagnosis, treatment, research, and medical procedures. Accordingly, as shown in FIG. 3, the GUI 300 can provide the user with tools (e.g., such as the selectable options 306 307) that allow the user to interact with the modelled version of the brain. The user can provide input for selecting portions of the processed data 302 to be displayed. The selected portions can be objects, e.g. brain parcellations, nodes, edges, that the medical professional desires to see more information about, remove from the brain in a simulated procedure, or otherwise review and analyze. The user can specify particular portions of the brain to analyze. The user may also desire to identify and specify, on the GUI 300, particular objects on several features, such as local properties of brain tissue, connectivity parameters, structural markers, functional markers, and/or the like. The disclosed technology therefore can provide the user with a more comprehensive, interactive, and user-friendly interface for making determinations about a particular brain's condition(s).

Figure 4:
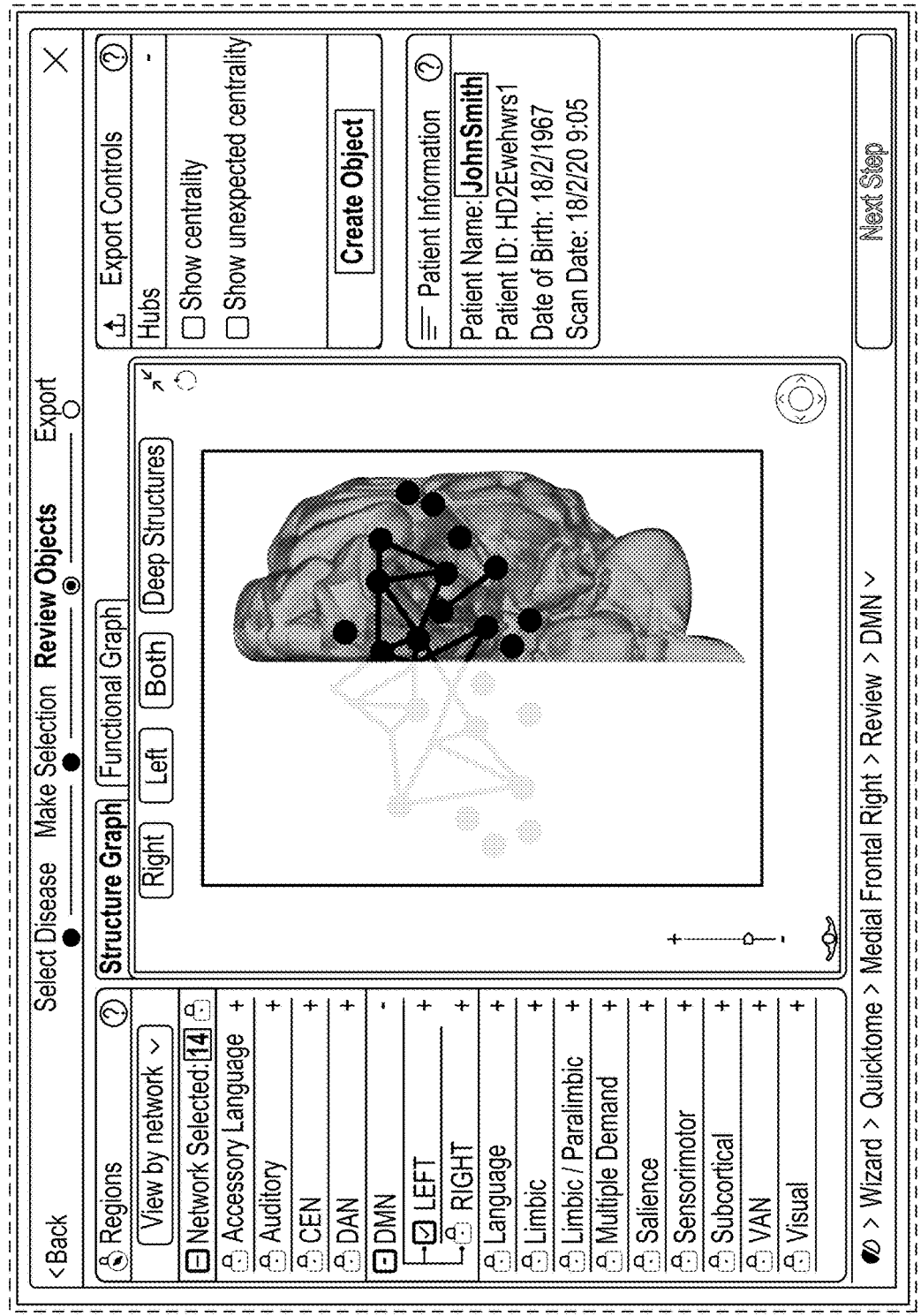
FIG. 4 illustrates an example user-interactive GUI displaying part of the brain in FIG. 3.
Figure 5:
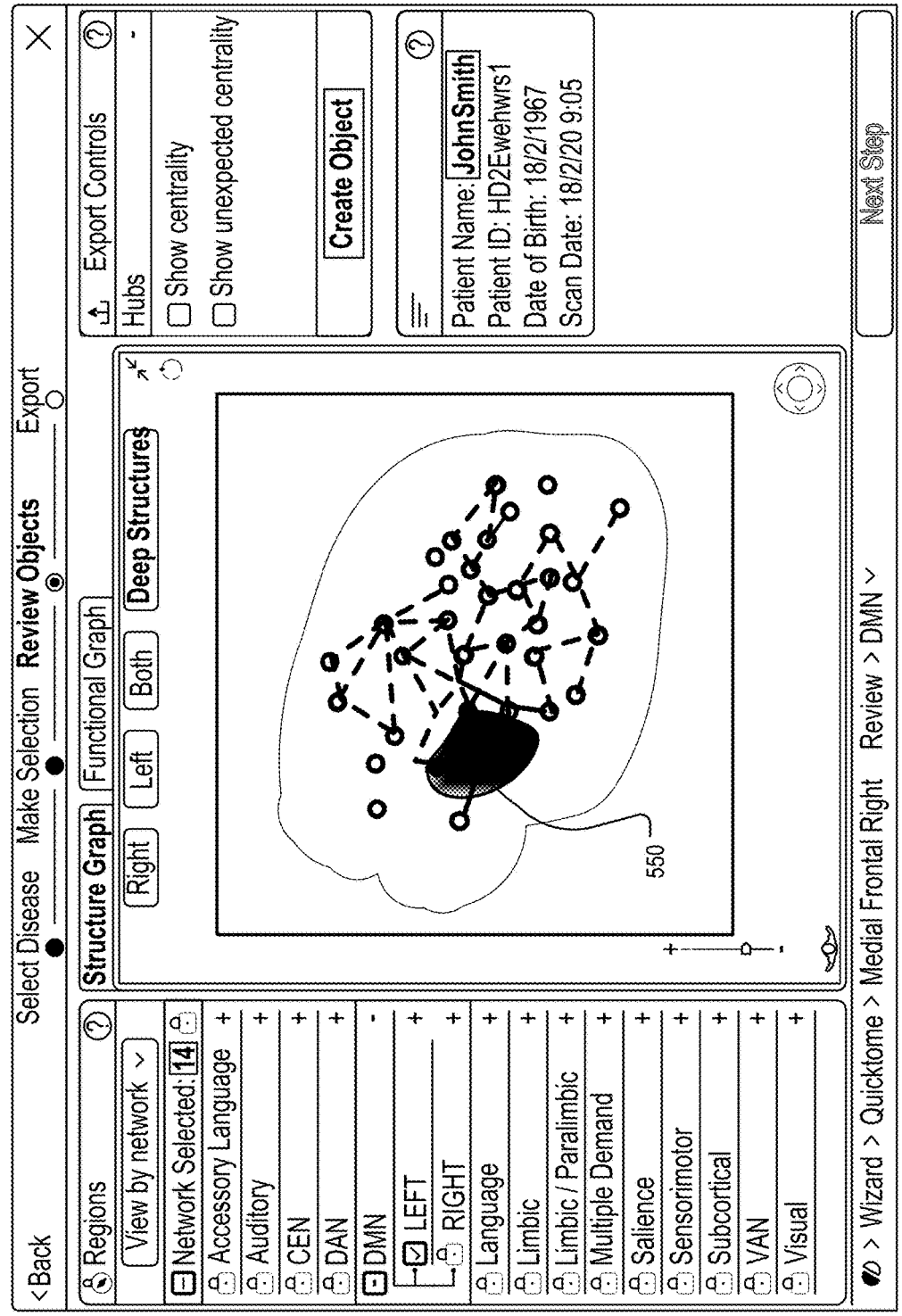
FIG. 5 illustrates an example user-interactive GUI displaying a deep structure of the brain in FIG. 3.

The user can use the selectable options 306 307 to specify particular actions (e.g. by making selections in the GUI 300 presented at the user device 104 via an input device) with regards to the processed data 302. For example, as shown in FIG. 4, the user can select to visualize left, right, or both sides of the brain for anatomical, connectivity information, or both using the GUI 400. As another example, the user can select to only visualize an area with structure and/or functional data within that area of the brain. Such an area can be deep beneath the surface of the brain. As shown in FIG. 5, the insula 550 of the brain is shown in the GUI 500 with other areas of the brain suppressed for focused and undisturbed visualization of the area deep within the brain.

The user can also choose options to export the processed data 30, for example, using an available network. The user can save the exported data (e.g., in the data store 108 in FIG. 1), which can be used in future research and analysis.

The GUI 300 presents only some options that may be presented to the user with regards to the processed data 302. One or more other options are also possible and can be presented in the GUI 300 and/or in additional GUIs that are outputted at the user device 104.

Moreover, as described herein, the GUI 300 can be part of a specialized computing system in the hospital IT infrastructure. Sometimes, the GUI 300 can also be accessible via a web browser. The GUI 300 may be configured, e.g. by authentication mechanisms such as login using username and/or password, biometric detection, and/or the like, to be used by only authorized individuals, such as clinicians (e.g. doctors, nurses, clinical staff, or the like), other medical professionals, or other authorized users (e.g. network administrator, technical staff, or the like) at the hospital or other medical setting. In some implementations, the GUI 300 can also be in communication with or otherwise linked to one or more external devices, such as remote computers, that can be used to facilitate brain surgery or other medical procedures.

Figure 6:
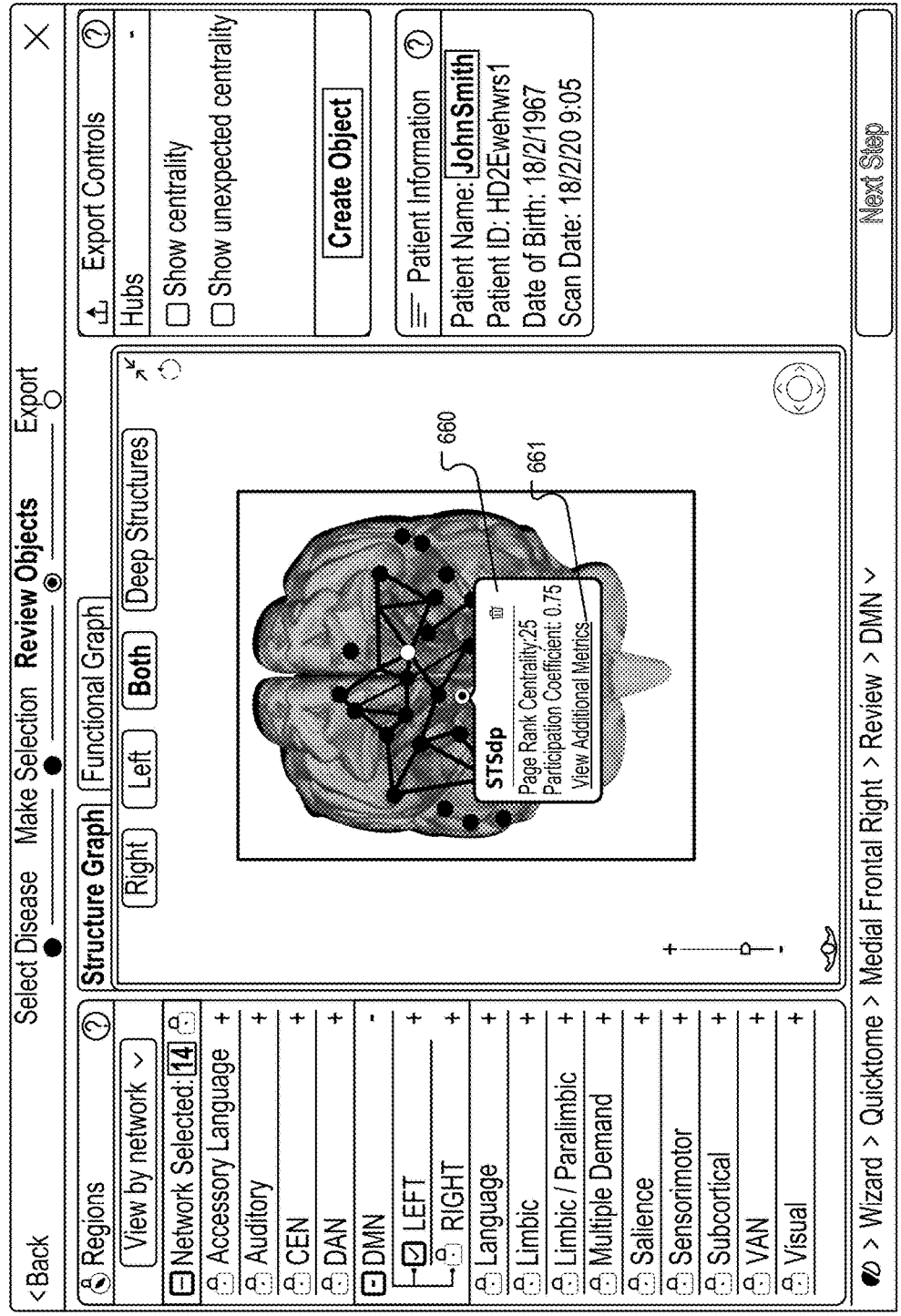
FIG. 6 illustrates an example user-interactive GUI displaying the brain superimposed with hub data.
Figure 7:
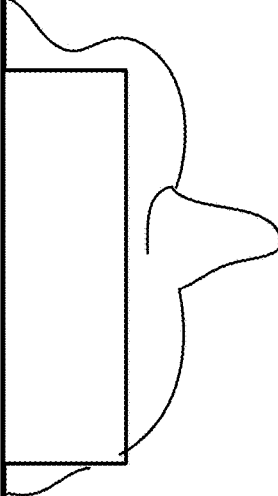
FIG. 7 illustrates an example user-interactive GUI displaying the hub data.

FIG. 6 is an example user-interactive GUI displaying the brain as shown in FIGS. 3-4. The GUI 600 can display visual representations of the brain including anatomical and connectivity information as shown in FIGS. 3-4, simultaneously. The connectivity information can include multiple nodes and edges that are spatially aligned to the anatomical structures of the brain. The nodes and edges may be displayed using a uniform pattern or color. Additionally, in response to detecting a user interaction with the GUI 600, for example, with one or more nodes or edges displayed on the GUI, a pop-up window 660 with one or more parameters or metrics related to the selected node(s) or edge(s) can be displayed on the GUI 600. Such parameters may be overlaid on the visual representations of the particular brain. The pop-up window can be in proximity to the selected node(s) or edge(s) on the GUI. The user may interact with the pop-up window to drag it to a different position, delete it, or click on one or more parameters listed thereon. In response to detecting a user interaction with the pop-up window 660, e.g., with a hyperlink of "view additional metrics," 661, the GUI 600 can display a second window 700 that includes additional parameters or metrics related to the user selection of node(s) or edge(s), as shown in FIG. 7. The second window can be in a separate window from the GUI 600.

The parameters and metrics can be part of and included in the connectivity data. The connectivity data may include the parameters and metrics with relation to one or more nodes and/or edges. The parameters and metrics can be related to the selected node(s) or edge(s). The parameters and metrics can include, but are not limited to, parameters and metrics for indicating connectivity, centrality, hubness, expected hubness, and unexpected hubness of the selected node(s) or edge(s). The parameters and metrics may also include classification of the node(s) and/or edge(s) as unexpected or expected relative to a population, e.g., a population with similar condition(s) as the patient examination. The parameters and metrics may also include classification of the node(s) and/or edge(s) as unexpected hubness with higher or lower than normal hubness.

The parameters and metrics may include a list of parameters and metrics, each parameter or metric including a name of parameter, a value of the parameter, with or without a unit.

For example, the parameters and metrics can include participation coefficients, which measures the distribution of edges that directly connect to a node. If a node's edges are more restricted to a smaller region of the brain, its participation coefficient is smaller than if the node's edges are evenly distributed among a larger region of the brain. Hubs or nodes with higher participation coefficients are more likely to be "connector" hubs than hubs or nodes with lower participation coefficients. The participation coefficient can be a measure of redundancy of an area, e.g., a node, in the brain.

The parameters and metrics can include centrality parameters, e.g., PageRank centrality. The PageRank centrality can include a score in a predetermined range, e.g., 1-379, with a higher score predicting a higher degree of eloquence. In some embodiments, higher scores in PageRank centrality can correspond with areas with hubness of the brain and "no-go" zones for neurosurgical interventions. PageRank centrality can be used to measure how connected an area, e.g., a node, is to the rest of the brain. PageRank centrality is described in more detail in Ahsan S A et al *Beyond eloquence and onto centrality: a new paradigm in planning supratentorial neurosurgery*. J Neurooncol 146(2):229-238.

The parameters and metrics can include graph theory analyses of the brain imaging data. For example, the centrality data can include betweenness centrality, which is a measure of centrality based on shortest paths between pairs of nodes. The betweenness centrality for each node may be the number of shortest paths that pass through the node. The betweenness centrality can be used to measure how connected an area, e.g., a node, is to the rest of the brain. As another example, the parameters and metrics can include clustering coefficient, which is a measure of the degree to which nodes tend to cluster together with other nodes of the brain. As yet another example, the parameters and metrics can include modularity, which is a measure that quantifies the extent to which the brain is divided into distinct subnetworks, or modules. The modularity and clustering coefficient can be a measure of redundancy of an area, e.g., a node, in the brain.

Figure 8:
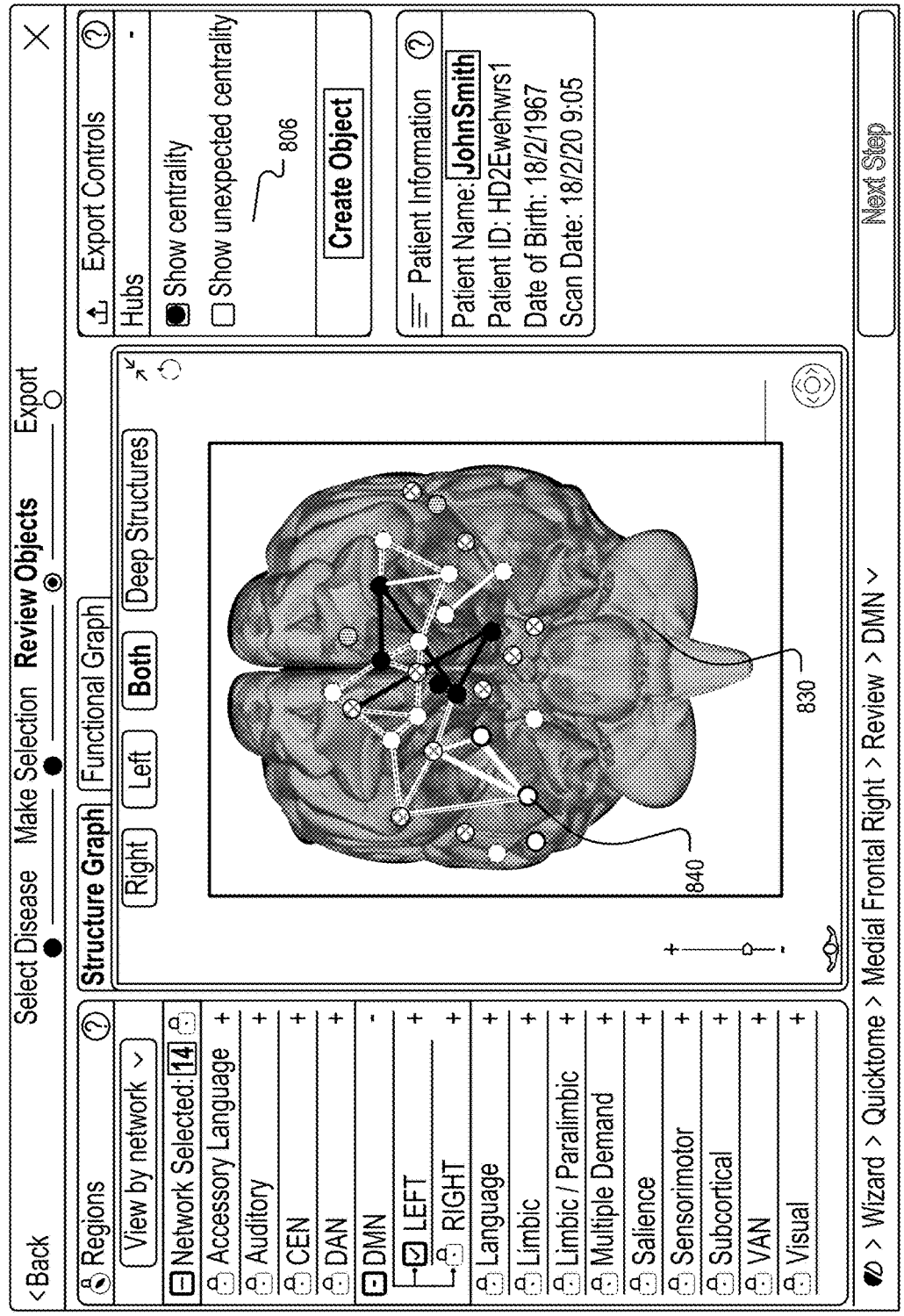
FIG. 8 illustrates an example user-interactive GUI displaying the brain superimposed with unexpected hub data.

FIG. 8 is an example user-interactive GUI of the particular brain as shown in FIGS. 3-6. In response to detecting a user interaction with the selectable options 806, more specifically, by selecting "show centrality" option 806 at the GUI 800, the centrality or hub data 840 of the brain is superimposed on the anatomical data 830 and also spatially registered with the anatomical data 830.

The centrality or hub data 840 may be color-coded with different colors to indicate different degrees of centrality for nodes and edges. Similarly, the centrality data may use different grayscales or patterns to indicate different degrees of centrality for nodes and edges. As shown in FIG. 8, the nodes are represented with five different combinations of grayscales and patterns to show different degrees of centrality. Similarly, the edges are also represented with white, black and two different types of dotted lines to indicate different degrees of centrality and hubness. Some or all of the degrees of centrality can be color-coded. Some or all of the degrees of centrality can be displayed with different grayscales and/or patterns. As such, the user can simultaneously visualize where the brain hubs are relative to brain structures and a qualitative distribution of hubs. For example, a user may use the displayed hubs to determine if there are nodes in proximity with each other that are of similar hubness or centrality.

The centrality data may be "raw" data without comparison to any reference centrality data. In other words, the centrality or connectivity information may be indicative of the degree of connectivity within the same brain. For example, a user can find nodes and edges that have more connectivity than other nodes and edges within the same brain. In some embodiments, one or more nodes and one or more edges may be displayed using a same color, grayscale, pattern, or any other visually perceivable characters.

Figure 9:
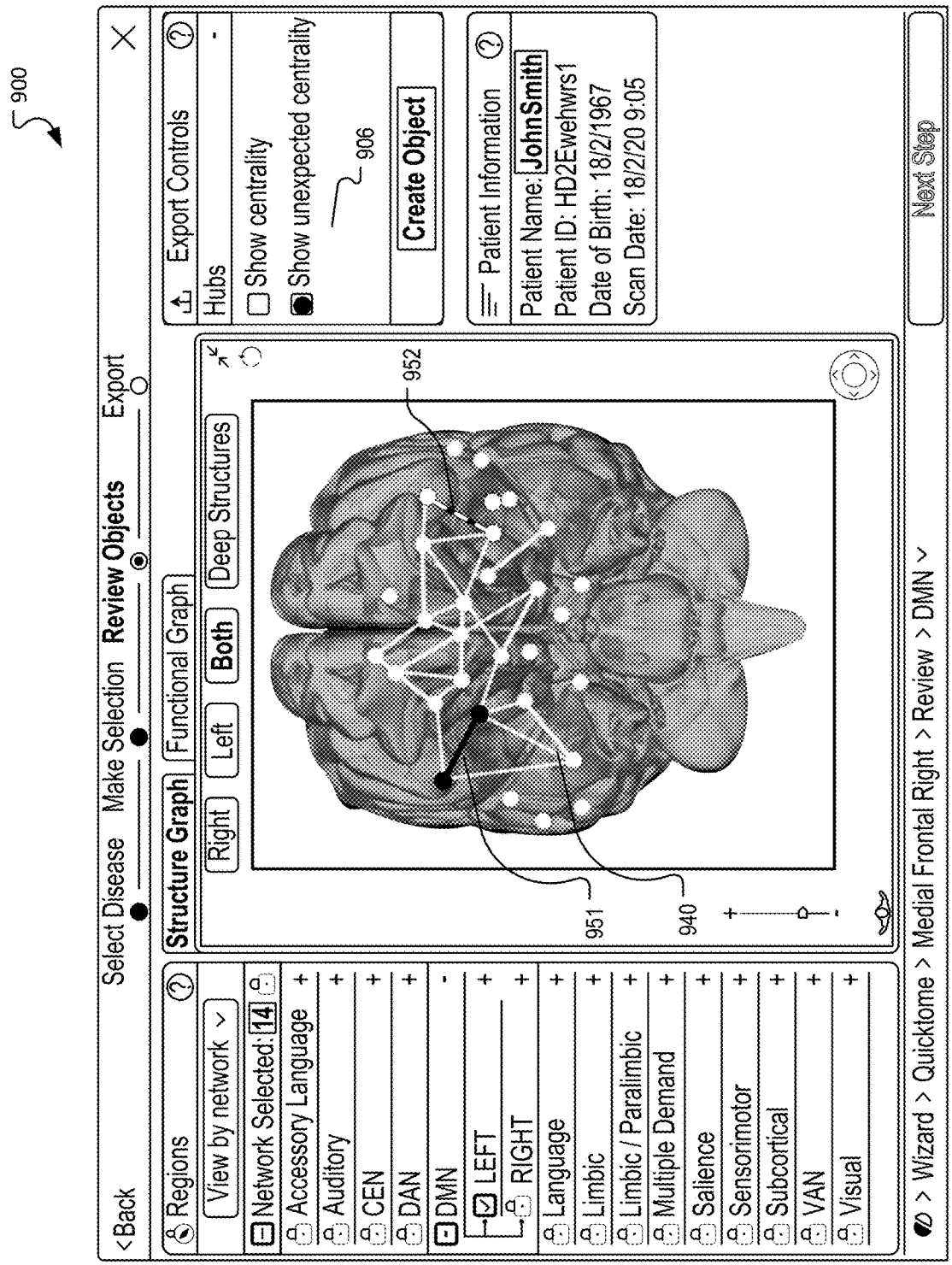
FIG. 9 illustrates an example user-interactive GUI displaying the brain superimposed with unexpected hub data.

FIG. 9 is an example user-interactive GUI of the particular brain as shown in FIG. 8. In response to detecting that the user interacts with the GUI 900 by selecting "show unexpected centrality" 906 at the GUI 900. The centrality or hub data 940 of the brain is superimposed on the anatomical data and also spatially registered with the anatomical data. The centrality or hub data can be color-coded differently based on the degree of centrality. Alternatively, the centrality or hub data can be of different grayscales, patterns, or other visually perceivable character based on the degree of centrality. For example, the nodes and edges of normal or expected centrality, e.g., within a predetermined centrality range, may have a first color, gray scale, or pattern that is different from those exhibiting unexpected centrality or hubness. The nodes and edges with unexpected centrality can be either above or below a reference centrality value or range. The reference centrality value or range can be equivalent to a specified threshold value or range. Different colors, grayscales, or and/or patterns can be used for centrality above and below the normal centrality data 951 952 to allow the user to conveniently visualize such data. The specific reference centrality can be predetermined or customized based on different clinical needs. For example, a reference centrality range can be obtained by averaging centrality data of subjects of a selected age, gender, medical condition, or any other grouping criteria. The reference centrality value or range can be associated with some or all portions of the brain. For example, the reference value or range can be only for comparable regions of different brains, and such regions may be defined using reference points or structures within the brains.

The visualization of unexpected centrality data 951, 952 using the GUI 900 can provide the user a combination of helpful information including but not limited to: unexpected centrality below a reference 951, unexpected centrality above a reference 952, a spatial location of each unexpected hub within the brain, the location of each unexpected hub with respect to anatomical structure(s) in the brain, the unexpected hubs in spatial relationship to other normal or unexpected hubs, and the unexpected edges between a pair of unexpected hubs.

Visualization of the centrality data and hub data including the unexpected hubness data using the technologies disclosed herein is fast, efficient, and easy to interpret for the users, e.g., clinicians or neurosurgeons. As a result, the user can perform improved and more informed diagnoses, treatments, operations, research, or their combinations than with any existing systems or technologies.

Figure 10:
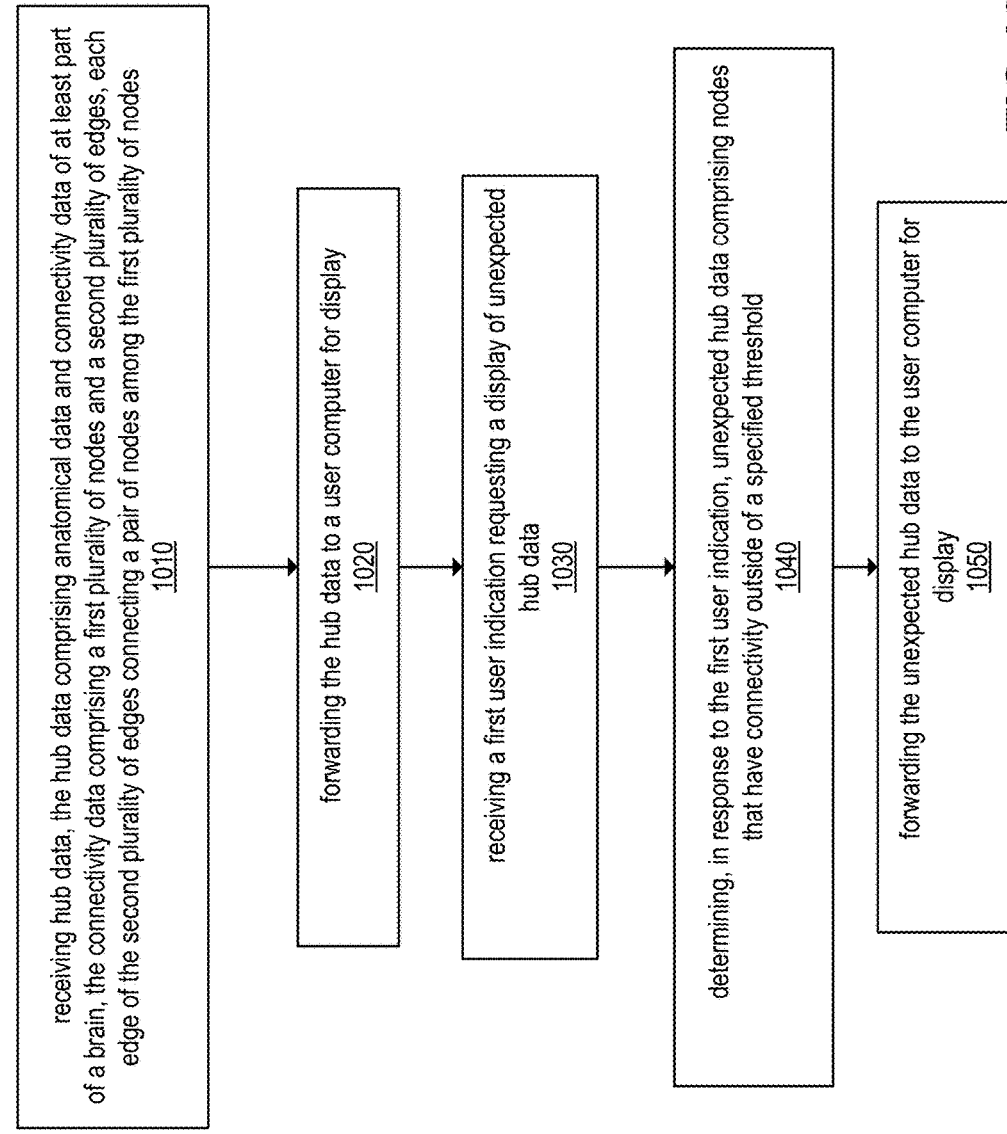
FIG. 10 illustrates an example process for enabling the user-interactive GUI to display hub data of the brain.

FIG. 10 is an example process of enabling display of brain hub data in relation to the brain anatomical data. The operations in FIG. 10 may be performed by the computer system 106 in FIGS. 1-2. The computer system may receive hub data from another computer or memory device such as the data store 108 in FIGS. 1-2 (1010). The hub data can include anatomical data and connectivity data of some or all portions of the brain. The connectivity data can include a first plurality of nodes and a second plurality of edges, and each edge of the second plurality of edges connects a pair of nodes among the first plurality of nodes. The anatomical data and the connectivity data can be spatially registered relative to each other. The registration can be performed by the computer system 106 in FIGS. 1-2.

The connectivity data of one or more of the nodes, edges, or their combinations may include hubness parameters and metrics. For example, a node can have a betweenness centrality of 5, a modularity of 15, and a clustering coefficient of 35. Such parameters and metrics may be calculated by the computer system 106 in FIGS. 1-2 or obtained from another computer or storage device such as the data store 108. The connectivity data of one or more of the nodes, edges, or their combinations may include a binary classification of the corresponding node or edge. For example, one node may be classified as "1" as an unexpected hub, or "0" as a normal hub. As another example, one node may be classified as higher centrality than normal or expected hubs or lower centrality than normal or unexpected hubs.

The computer system may forward the hub data to a user computer for display 1020. The display can include spatially registered anatomical data and connectivity data. The connectivity data can be superimposed on the anatomical data. The computer system may forward part of the hub data based on the user's indication so as to save data transmission bandwidth and transmission time.

After the hub data is displayed at the user computer, for example, using a digital display, the user may interact with the hub data via a user-interactive GUI display at the digital display of the user computer. The computer system can receive a user interaction with the GUI 1030, e.g., an indication requesting a display of unexpected hub data.

In response to receiving the user interaction with the GUI, the computer system can determine the unexpected hub data 1040, using a computer program, a software, or the like that is executable on the computer system. The unexpected hub data may include nodes, edges, or both that have centrality parameters that are outside a specified threshold. The specified threshold can be a single value or a range encompassing multiple values. The specified threshold can be predetermined and obtained by the computer system. For example, a specified threshold can be calculated based on inputs provided by the user. As another example, the specified threshold can be calculated by the computing system automatically using a computer program or software based on patient information as its input(s). The threshold can be calculated in various ways. As an example, the specified threshold can be calculated across a population of subjects. As another example, the specified threshold can be calculated in comparison to centrality values for that particular subject, e.g., the threshold can be set as above top 10% of centrality values. As yet another example, the specified threshold can also be calculated based on a standard deviation from the centrality values of the particular subject. The specified threshold can also be a function of the patient information including but not limited to age, gender and other biological factors.

The patient information can include but is not limited to age, gender, brain disease, treatment, and symptom. The specific threshold may indicate normal or expected centrality of nodes and/or edges. The specific threshold may be with regard to a single parameter or metric related to centrality or hubness. The unexpected hub data includes nodes, edges, or their combination whose value or range of the corresponding single parameter is outside the specified threshold. Alternatively, the specified threshold may include a list of specified values or ranges, each corresponding to a different parameter or metric. The unexpected hub data are nodes, edges, or their combination whose values or ranges of parameters are outside the list of specified values or ranges. Determining the unexpected hub data may include calculating a classification for each node and edge included in the hub data. Such classification can be stored in association with the corresponding node or edge by the computing system in a computer memory device such as the data store 108.

After the unexpected hub data is determined, the computer system can forward such data to the user's device for display 1050. The display may include colors, patterns, or greyscales for the unexpected hub data that are different from the expected or normal hubs. The display may include superimposing the unexpected hub data on the anatomical data of the brain. The display may be customized by the user to suppress normal or expected hub data and only show the unexpected hub data. The display may include two different colors, greyscales, or patterns, one representing unexpected hub data with centrality parameter(s) higher than those of the normal or expected hub data, the other representing unexpected hub data with centrality parameter(s) smaller than those of the normal or expected hub data. In some cases, the unexpected hubness data may be displayed with different color or gray scales to indicate how different it is from the normal hubness value or range. For example, the GUI may include a color bar or a greyscale bar so that unexpected hubs above the threshold are displayed with different colors or greyscales to indicate the extent that a node or edge is different from the specified range. The user may also customize the visualization of unexpected hubness data in relation to expected hubness data and/or other unexpected hub data within a selected region of the brain.

One implementation of the invention disclosed herein is an example process of enabling display of brain hub data in relation to the brain anatomical data. The operations may be performed by the user device 104 or computer system 106 in FIGS. 1-2. The device may receive hub data from another computer or memory device such as the data store 108 in FIGS. 1-2. The hub data can include anatomical data and connectivity data of some or all portions of the brain. The connectivity data can include a first plurality of nodes and a second plurality of edges, and each edge of the second plurality of edges connects a pair of nodes among the first plurality of nodes. The anatomical data and the connectivity data can be spatially registered relative to each other.

The user device 104 may display the hub data using a digital display using a GUI. The user may interact with the hub data via the GUI. The user device 104 can receive a user interaction with the GUI, e.g., an indication requesting a display of unexpected hub data.

In response to receiving the user interaction with the GUI, the user device can determine the unexpected hub data. The unexpected hub data may include nodes, edges, or both that have centrality parameters that are outside a specified threshold or range. The specific threshold or range may indicate normal or expected centrality of nodes and/or edges. The unexpected hub data may include nodes, edges, or both that have been classified as unexpected.

After the unexpected hub data is determined, the user device can display such data. The display may include different colors of the unexpected hub data from other data in the hub data. The display may include superimposing the unexpected hub data on the anatomical data of the brain. The display may include suppressing normal or expected hub data and only show the unexpected hub data. The display may include two different colors, one color representing unexpected hub data with centrality parameter(s) higher than those of the normal or expected hub data, the other color representing unexpected hub data with centrality parameter(s) smaller than those of the normal or expected hub data.

Figure 11:
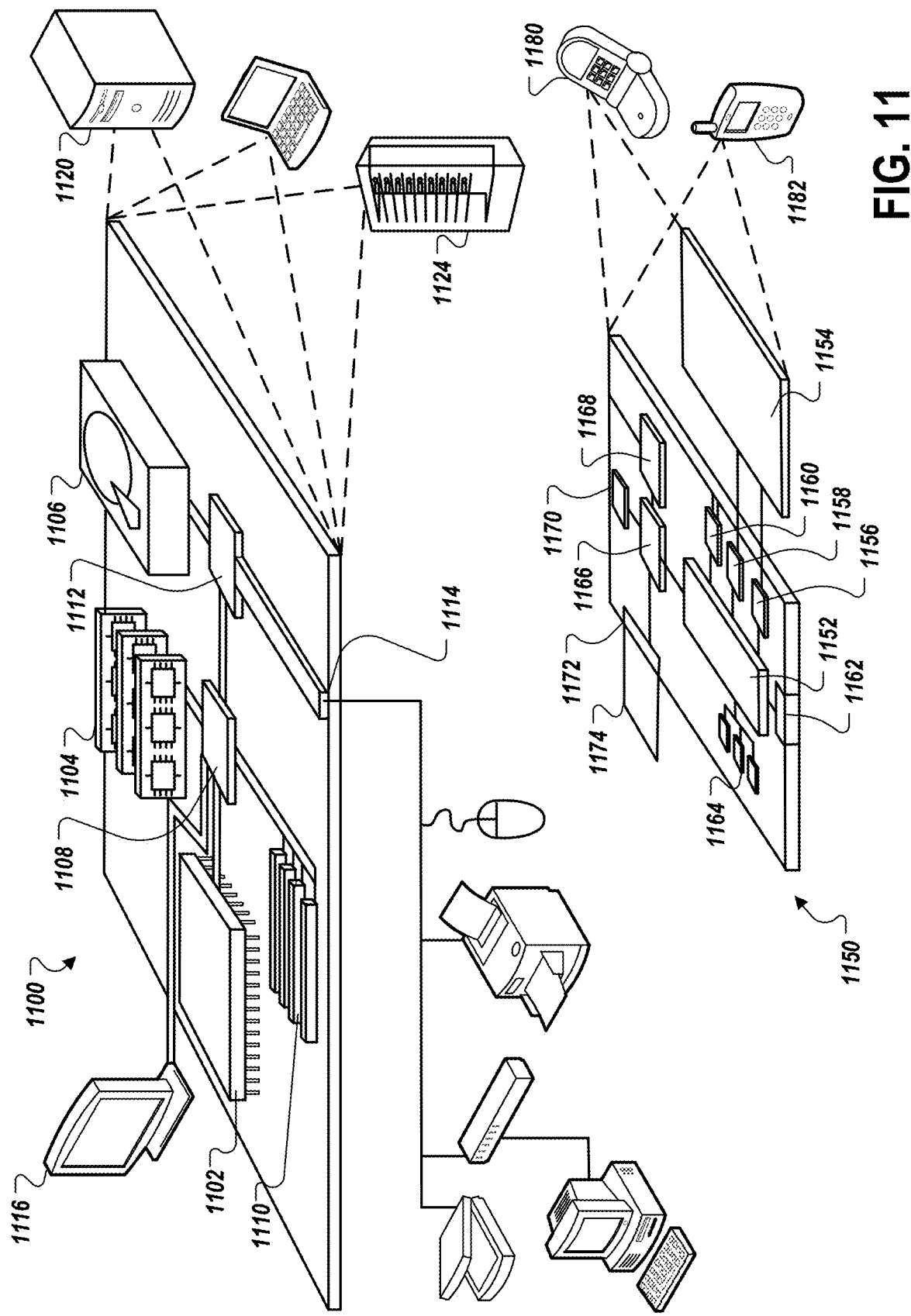
FIG. 11 is a schematic diagram that shows an example of a computing device and a mobile computing device.

FIG. 11 shows an example of a computing device 1100 and an example of a mobile computing device that can be used to implement the techniques described here. The computing device 1100 can be the computer system 106 or user device 104 in FIGS. 1-2. The computing device 1100 can be various forms of digital computers, such as laptops, desktops, workstations, personal digital assistants, servers, blade servers, mainframes, and other appropriate computers. The mobile computing device is intended to represent various forms of mobile devices, such as personal digital assistants, cellular telephones, smart-phones, and other similar computing devices. The components shown here, their connections and relationships, and their functions, are meant to be exemplary only, and are not meant to limit implementations of the inventions described and/or claimed in this document.

The computing device 1100 includes a processor 1102, a memory 1104, a storage device 1106, a high-speed interface 1108 connecting to the memory 1104 and multiple high-speed expansion ports 1110, and a low-speed interface 1112 connecting to a low-speed expansion port 1114 and the storage device 1106. Each of the processor 1102, the memory 1104, the storage device 1106, the high-speed interface 1108, the high-speed expansion ports 1110, and the low-speed interface 612, are interconnected using various busses, and can be mounted on a common motherboard or in other manners as appropriate. The processor 1102 can process instructions for execution within the computing device 1100, including instructions stored in the memory 1104 or on the storage device 1106 to display graphical information for a GUI on an external input/output device, such as a display 1116 coupled to the high-speed interface 1108. In other implementations, multiple processors and/or multiple buses can be used, as appropriate, along with multiple memories and types of memory. Also, multiple computing devices can be connected, with each device providing portions of the necessary operations (e.g., as a server bank, a group of blade servers, or a multi-processor system).

The memory 1104 stores information within the computing device 1100. The memory 1104 can also be another form of computer-readable medium, such as a magnetic or optical disk.

The storage device 1106 is capable of providing mass storage for the computing device 1100. In some implementations, the storage device 1106 can be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product can also contain instructions that, when executed, perform one or more methods, such as those described above. The computer program product can also be tangibly embodied in a computer- or machine-readable medium, such as the memory 1104, the storage device 1106, or memory on the processor 1102.

The high-speed interface 1108 manages bandwidth-intensive operations for the computing device 1100, while the low-speed interface 612 manages lower bandwidth-intensive operations. Such allocation of functions is exemplary only.

The computing device 1100 can be implemented in a number of different forms. For example, it can be implemented as a standard server 1120, or multiple times in a group of such servers. In addition, it can be implemented in a personal computer such as a laptop computer 1122. It can also be implemented as part of a rack server system 1124. Alternatively, components from the computing device 1100 can be combined with other components in a mobile device (not shown), such as a mobile computing device 1150. Each of such devices can contain one or more of the computing device 1100 and the mobile computing device 1150, and an entire system can be made up of multiple computing devices communicating with each other.

The mobile computing device 1150 includes a processor 1152, a memory 1164, an input/output device such as a display 1154, a communication interface 1166, and a transceiver 1168, among other components. The mobile computing device 1150 can also be provided with a storage device, such as a micro-drive or other device, to provide additional storage. Each of the processor 1152, the memory 1164, the display 1154, the communication interface 1166, and the transceiver 1168, are interconnected using various buses, and several of the components can be mounted on a common motherboard or in other manners as appropriate.

The processor 1152 can execute instructions within the mobile computing device 1150, including instructions stored in the memory 1164. The processor 1152 can communicate with a user through a control interface 1158 and a display interface 1156 coupled to the display 1154. The display 1154 can be, for example, a TFT (Thin-Film-Transistor Liquid Crystal Display) display or an OLED (Organic Light Emitting Diode) display, or other appropriate display technology. The display interface 1156 can comprise appropriate circuitry for driving the display 1154 to present graphical and other information to a user. The control interface 1158 can receive commands from a user and convert them for submission to the processor 1152. In addition, an external interface 1162 can provide communication with the processor 1152, so as to enable near area communication of the mobile computing device 1150 with other devices. The external interface 662 can provide, for example, for wired communication in some implementations, or for wireless communication in other implementations, and multiple interfaces can also be used.

The memory 1164 stores information within the mobile computing device 1150. The memory 1164 can be implemented as one or more of a computer-readable medium or media, a volatile memory unit or units, or a non-volatile memory unit or units.

The memory can include, for example, flash memory and/or NVRAM memory (non-volatile random access memory), as discussed below. In some implementations, a computer program product is tangibly embodied in an information carrier. The computer program product contains instructions that, when executed, perform one or more methods, such as those described above. The computer program product can be a computer- or machine-readable medium, such as the memory 1164, the expansion memory 1174, or memory on the processor 1152. In some implementations, the computer program product can be received in a propagated signal, for example, over the transceiver 1168 or the external interface 1162.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other. In some implementations, the computing system can be cloud based and/or centrally processing data. In such cases, anonymous input and output data can be stored for further analysis. In a cloud based and/or processing center set-up, compared to distributed processing, it can be easier to ensure data quality, and accomplish maintenance and updates to the calculation engine, compliance to data privacy regulations and/or troubleshooting.

While this specification contains many specific implementation details, these should not be construed as limitations on the scope of the disclosed technology or of what may be claimed, but rather as descriptions of features that may be specific to particular embodiments of particular disclosed technologies. Certain features that are described in this specification in the context of separate embodiments can also be implemented in combination in a single embodiment in part or in whole. Conversely, various features that are described in the context of a single embodiment can also be implemented in multiple embodiments separately or in any suitable subcombination. Moreover, although features may be described herein as acting in certain combinations and/or initially claimed as such, one or more features from a claimed combination can in some cases be excised from the combination, and the claimed combination may be directed to a subcombination or variation of a subcombination. Similarly, while operations may be described in a particular order, this should not be understood as requiring that such operations be performed in the particular order or in sequential order, or that all operations be performed, to achieve desirable results. Particular embodiments of the subject matter have been described. Other embodiments are within the scope of the following claims.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non-transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially-generated propagated signal, e.g., a machine-generated electrical, optical, or electromagnetic signal that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application-specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, an app, a module, a software module, a script, or code, can be written in any form of programming language, including compiled or interpreted languages, or declarative or procedural languages; and it can be deployed in any form, including as a stand-alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a data communication network.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone, running a messaging application, and receiving responsive messages from the user in return.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface, a web browser, or an app through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML, page, to a user device, e.g., for purposes of displaying data to and receiving user input from a user interacting with the device, which acts as a client. Data generated at the user device, e.g., a result of the user interaction, can be received at the server from the device.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

What is claimed is:

1. A method comprising:
   receiving hub data, the hub data comprising anatomical data and connectivity data of at least part of a brain, the connectivity data comprising a first plurality of nodes and a second plurality of edges, each edge of the second plurality of edges connecting a pair of nodes among the first plurality of nodes;
   forwarding the hub data to a user computer for display;
   receiving a first user indication requesting a display of unexpected hub data;
   determining, in response to the first user indication, unexpected hub data comprising nodes that have connectivity outside of a specified threshold; and
   forwarding the unexpected hub data to the user computer for display.

2. The method of claim 1, wherein receiving the hub data comprises determining the connectivity data and spatially registering the anatomical data with the connectivity data.

3. The method of claim 1, wherein the anatomical data comprises a brain atlas, a glass brain, a plurality of images obtained using a medical imaging device, or a combination thereof, and wherein one or more nodes or edges comprises a plurality of hubness parameters.

4. The method of claim 1, wherein each node of the first plurality of nodes is a parcellation comprising one or more voxels in a medical image of the brain.

5. The method of claim 1, wherein each edge of the second plurality of edges comprises multiple fiber tracts.

6. The method of claim 1, wherein the connectivity data represents a degree of correlation of activity between a selected node and one or more other nodes of the first plurality of nodes.

7. The method of claim 1, wherein the nodes that have connectivity outside of the specified threshold comprises the nodes having connectivity below the specified threshold.

8. The method of claim 1, wherein the nodes that have connectivity outside of the specified threshold comprises the nodes having connectivity above the specified threshold.

9. The method of claim 1, wherein the anatomical data and the connectivity data are in three dimensions (3D), and the hub data comprises 3D data.

10. The method of claim 1, wherein the unexpected hub data comprises 3D data.

11. The method of claim 10, wherein the unexpected hub data further comprises one or more quantitative or qualitative parameters associated with a node, an edge, or a combination thereof.

12. The method of claim 1, wherein the connectivity data comprises a binary classification for each of the first plurality of nodes.

13. The method of claim 12, wherein the unexpected hub data includes only nodes that are classified as unexpected.

14. The method of claim 1, wherein the displayed unexpected hub data is used by a user to make a clinical judgement or decision, comprising one or more of:
guiding a surgical procedure; predicting an outcome of the surgical procedure; evaluating risk associated with the surgical procedure; selecting appropriate target for a therapy; and understanding nature of a neurologic deficit in a subject.

15. The method of claim 1 further comprising:
receiving a user interaction with the display of the unexpected hub data;
determining, in response to the user interaction, an update on the unexpected hub data; and
forwarding the update to the user computer for an updated display.

16. The method of claim 15, wherein the update on the unexpected hub data comprises only a portion of the unexpected hub data.

17. The method of claim 15, wherein the update on the unexpected hub data comprises: a zoom-in of the unexpected hub data, a rotation of the unexpected hub data, a display of a parameter corresponding to a selected node or edge, a change of color of at least part of the unexpected hub data, or a combination thereof.

18. The method of claim 1, wherein the connectivity data have been spatially registered with the anatomical data, the anatomical data describing anatomy of the at least part of the brain.

19. The method of claim 18, wherein the first plurality of nodes have specified locations within the anatomy of the at least a part of the brain.

20. A computer program product, encoded on one or more non-transitory computer storage media, comprising instructions that when executed by one or more computers cause the one or more computers to perform operations comprising:
receiving hub data, the hub data comprising anatomical data and connectivity data of at least part of a brain, the connectivity data comprising a first plurality of nodes and a second plurality of edges, each edge of the second plurality of edges connecting a pair of nodes among the first plurality of nodes, the anatomical data and the connectivity data being spatially registered relative to each other;
forwarding the hub data to a user computer for display;
receiving a first user indication requesting a display of unexpected hub data;
determining, in response to the first user indication, unexpected hub data comprising nodes that have connectivity outside of a specified threshold; and
forwarding the unexpected hub data to the user computer for display.

21. One or more non-transitory computer storage media encoded with computer program instructions that when executed by one or more computers cause the one or more computers to perform operations comprising:
receiving hub data, the hub data comprising anatomical data and connectivity data of at least part of a brain, the connectivity data comprising a first plurality of nodes and a second plurality of edges, each edge of the second plurality of edges connecting a pair of nodes among the first plurality of nodes, the anatomical data and the connectivity data being spatially registered relative to each other;
forwarding the hub data to a user computer for display;
receiving a first user indication requesting a display of unexpected hub data;
determining, in response to the first user indication, unexpected hub data comprising nodes that have connectivity outside of a specified threshold; and
forwarding the unexpected hub data to the user computer for display.

22. A system comprising:
one or more computers and one or more storage devices on which are stored instructions that are operable, when executed by the one or more computers, to cause the one or more computers to perform operations comprising:
receiving hub data, the hub data comprising anatomical data and connectivity data of at least part of a brain, the connectivity data comprising a first plurality of nodes and a second plurality of edges, each edge of the second plurality of edges connecting a pair of nodes among the first plurality of nodes, the anatomical data and the connectivity data being spatially registered relative to each other;
forwarding the hub data to a user computer for display;
receiving a first user indication requesting a display of unexpected hub data;
determining, in response to the first user indication, unexpected hub data comprising nodes that have connectivity outside of a specified threshold; and
forwarding the unexpected hub data to the user computer for display.

* * * * *